(12) United States Patent
Williams

(10) Patent No.: US 7,077,522 B2
(45) Date of Patent: Jul. 18, 2006

(54) SHARPNESS METRIC FOR VISION QUALITY

(75) Inventor: David R. Williams, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/428,159

(22) Filed: Aug. 29, 2003

(65) Prior Publication Data

US 2004/0008323 A1    Jan. 15, 2004

Related U.S. Application Data

(60) Provisional application No. 60/377,219, filed on May 3, 2002.

(51) Int. Cl.
*A61B 3/00* (2006.01)
*A61B 3/10* (2006.01)

(52) U.S. Cl. .................. 351/246; 351/200; 351/205; 351/211; 351/221; 351/222

(58) Field of Classification Search ................ 351/200, 351/205, 206, 211, 221, 222, 246; 600/558; 128/922
See application file for complete search history.

(56) References Cited

U.S. PATENT DOCUMENTS 6,338,559 B1    1/2002  Williams et al.
6,511,180 B1    1/2003  Guirao et al.
6,634,751 B1 *  10/2003 Turner et al. ............... 351/212
6,722,767 B1 *  4/2004  Dick et al. .................. 351/211
6,761,454 B1 *  7/2004  Lai et al. .................... 351/216

OTHER PUBLICATIONS

Williams, D.R. Assessment of Optical Aberrrations of the Eye: Wavefront Sensing and Adaptive Optics., ARVO, Ft. Lauderdale, FL, May 2002.
Williams, D.R. Subjective Image Quality Metrics from the Wave Aberration. 4th International Congress of Wavefront Sensing and Aberration-Free Refractive Correction, San Francisco, CA, Feb. 16, 2003.
Williams, D.R. Predicting Subjective Image Quality from the Wave Aberration. ASCRS, San Francisco, CA, Apr. 12, 2003.

* cited by examiner

*Primary Examiner*—Patricia Bianco
*Assistant Examiner*—John R Sanders
(74) *Attorney, Agent, or Firm*—Blank Rome LLP

(57) ABSTRACT

A vision metric, called the sharpness metric, indicates the subjective sharpness of a patient's vision by taking into account both the wavefront aberration and the retinal response to the image. A retinal image quality function such as the point spread function is convolved by a neural quality function, and the maximum of the convolution over the retinal plane provides the sharpness metric. The sharpness metric can be used to control eye surgery or the fabrication of a lens.

20 Claims, 13 Drawing Sheets

STANDARD ABERRATION

TEST MODE

PATIENT WAVE ABERRATION

DEFOCUS

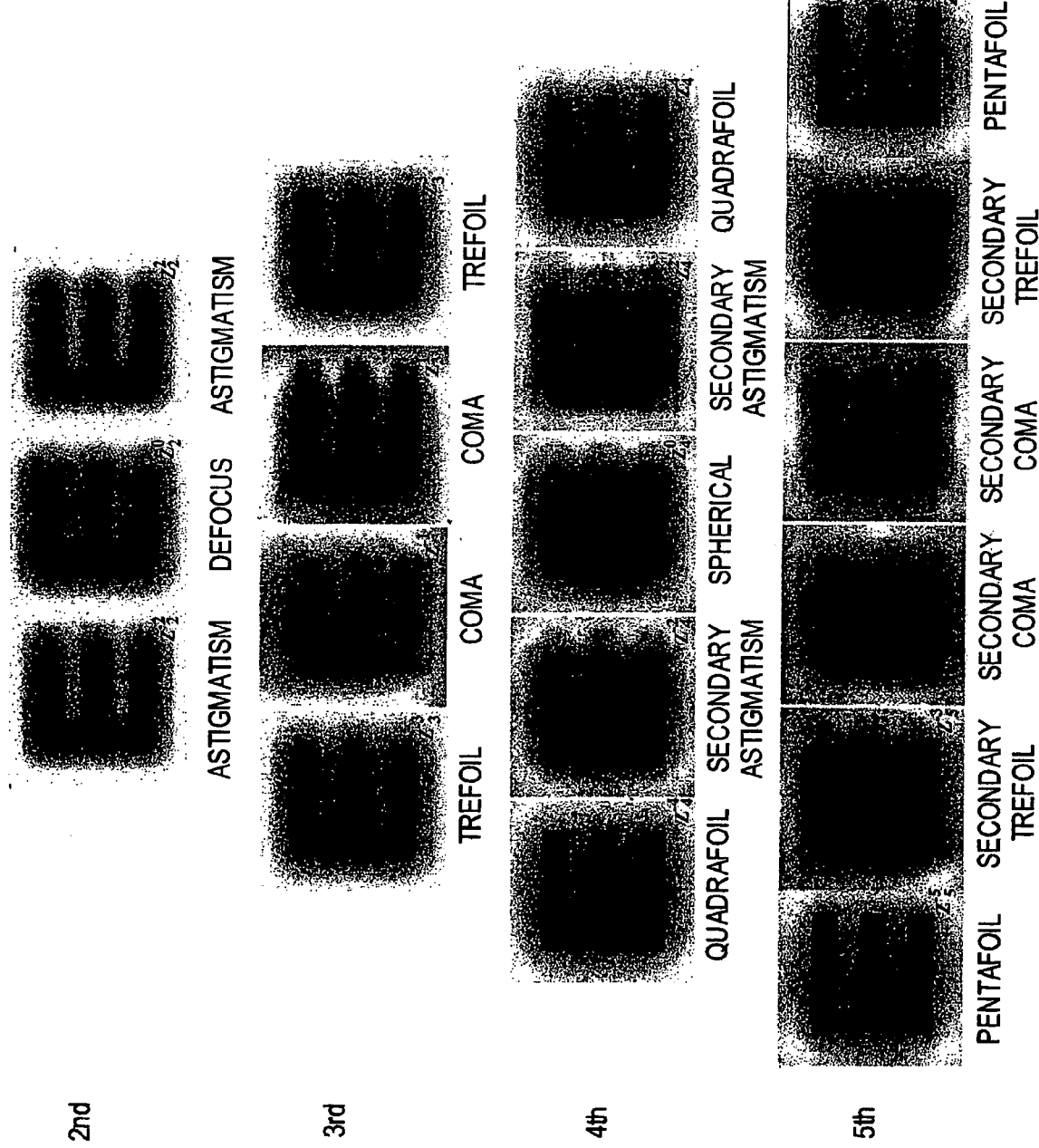

US 7,077,522 B2

SHARPNESS METRIC FOR VISION QUALITY

REFERENCE TO RELATED APPLICATION

The present application claims the benefit of U.S. Provisional Application No. 60/377,219, filed May 3, 2002, whose disclosure is incorporated by reference in its entirety into the present disclosure.

STATEMENT OF GOVERNMENT INTEREST

The research leading to the present invention was supported in part by NSF Science and Technology Center for Adaptive Optics grant number 5-24182. The government has certain rights in the present invention.

DESCRIPTION OF RELATED ART

The advent of rapid, automated wave front sensing in the eye now provides the clinician with a much richer description of the optics of each patient's eye than has been available before. Numerous methods have been developed to measure the wave aberration, some of which are objective, such as the Shack-Hartmann wavefront sensor, while others are subjective, such as the spatially resolved refractometer. In either case, these devices measure only optical characteristics of the eye. But vision depends on neural factors as well as optical ones. As the technology for measuring the wave aberration matures, there is a parallel effort to discover better ways of using the wave aberration to improve vision. A key issue is how to transform the wave aberration into a succinct description of how it will affect the patient's vision.

U.S. Pat. No. 6,511,180, issued Jan. 28, 2003, showed that metrics defined in the retinal image plane were superior to metrics based directly on the wave aberration defined in the pupil plane. Image plane metrics are generally preferred because they incorporate the process of image formation that occurs in the patient whose refraction is in question.

The ubiquitous practice today is to rely on the patient's responses to refract the eye. These measurements are time-consuming with a typical subjective refraction taking about 5 minutes per eye to perform. A wave front sensor measurement can be performed in a matter of seconds. A conventional refraction involves adjusting only three aberrations simultaneously to optimize visual performance. However, wave front technology allows many more than three aberrations to be corrected. A subjective procedure to identify the best values of more than three aberrations is probably not practical in a clinical setting. For this reason, higher order corrections must depend on algorithms to optimize vision rather than on the subjective response of the patient. Moreover, conventional refraction is subject to the variability inherent in the patient's response. If an objective metric could be developed that adequately mimics the behavior of the average visual system, it may be possible to reduce the variability in the refraction process and achieve a better visual outcome.

The wave aberration can be broken down into individual aberrations, or Zernike modes, with a process called Zernike decomposition. By analogy with the success in chemistry of reducing molecules to their atomic constituents, it is tempting to think that reducing the wave aberration to its fundamental components might provide the path to subjective image quality. Zernike decomposition can provide valuable insight into the relative importance of different aberrations for vision. It is useful in diagnosing the cause of a wave aberration and visual complaints. For example, a refractive surgery patient who post-op presents with an increase of vertical coma and complains of a vertical flare on car headlights at night very likely suffered some vertical decentration during laser ablation.

Though Zernike decomposition can provide insight into the effect of the wave aberration on vision, it is not especially useful in developing quantitative metrics. The reason for this is that Zernike modes can interact strongly with each other. Their subjective effects do not add together in a simple way. FIG. 1 provides an example. Shown are the retinal images of the letter E for three hypothetical eyes, one suffering only from defocus, one suffering from spherical aberration, and one suffering from both defocus and spherical aberration in the same amounts as present in the first two eyes. (When adding aberrations, it is the variance, which is the rms squared, that adds, not the rms itself. For example, in this case $0.5^2 + 0.16^2 = 0.52^2$). Strikingly, the image quality is obviously best in the eye that suffers from both aberrations rather than the eyes than suffer from only one of them. Measurements of the interactions between Zernike modes have shown that pairs of aberrations can sometimes increase acuity more than would be expected from the individual components or they can sometimes lead to a larger reduction in acuity than expected. Modes two radial orders apart and having the same sign and angular frequency (e.g., $C_2^0 + C_4^0$) tend to combine to increase visual acuity compared to loading the same magnitude RMS error into either component individually. Modes within the same radial order (e.g., $C_4^{-4} + C_4^0$) tend to combine to decrease acuity compared to loading the same magnitude RMS error into either component individually. The complexity of the interactions between Zernike modes in subjective blur means that Zernike decomposition, while useful for diagnosing the causes of aberrations, is not a productive avenue for deriving a metric of subjective image quality.

Wavefront sensors provide a physical measure of the severity of each patient's wave aberration in the form of the rms wavefront error. The RMS wavefront error is the square root of the sum of the squares of the deviation of the actual wavefront from the ideal wavefront. Unfortunately, rms wavefront error is not an especially useful metric for describing the subjective impact of the eye's wave aberration. FIG. 1 shows that the eye with the best image quality can sometimes have the highest RMS.

SUMMARY OF THE INVENTION

It will be readily apparent from the above that a need exists in the art for an improved metric for vision quality.

It is therefore an object of the invention to provide such a metric.

It is a further object of the invention to provide such a metric which is biologically plausible.

It is a still further object of the invention to provide such a metric which takes into account the neural response to the retinal image as well as the optical response (e.g., the eye's point spread function).

To achieve the above and other objects, the present invention is directed to a sharpness metric. The sharpness metric is the maximum of the convolution of the point spread function (PSF) measured in the retinal plane and a neural point spread function (PSF). The neural PSF can be modeled as a Gaussian function.

The metric is constructed according to the following principles. The number of metrics that one might explore to predict subjective image quality is infinite. To make this problem tractable, one must apply logical constraints that restrict the search to those domains that are most likely to yield the best solutions. The metrics proposed so far have involved summary statistics of the wave aberration itself, as defined in the pupil plane of the eye. However, there are sound reasons to adopt an entirely different approach. Metrics defined in the pupil plane, such as RMS, ignore all the processing that occurs subsequently despite the fact that we know enough about much of this processing to include it in a metric. Ultimately, we wish to know the effect of the wave aberration on the patient's vision. We seek a fast algorithm that replicates the optical and neural processes that occur within the patient as closely as possible. We propose that the principle for guiding the search for the best metric should be biological plausibility. That is, the more realistically the model captures the processing stages in the human visual system, the more likely the metric will be successful. For example, the optics of the eye form a retinal image through a process that is well understood and can be accurately described mathematically. The retinal image is then processed by a nervous system, the imaging properties of which are also reasonably well understood. Surely, the best metrics will mimic those steps that the patient's eye and brain actually take in order to see. The strength of building the metric around a model of vision is that additional factors can be added to the model as their significance is assessed. For example, the model might initially incorporate only the blurring effects of aberrations and diffraction on the retinal image, but experiments undertaken to see if light scatter and apodization by the Stiles-Crawford effect are important might increase predictive power.

The metric according to the present claimed invention illustrates the value of including neural as well as optical factors in predicting subjective image quality.

The results of our analysis so far supports the principle that metrics based on the optical and neural processes known to occur in human vision are superior to those based on the wave aberration alone. It seems highly likely that improvements in metric performance will be realized by building additional features into the model of human vision. For example, it is known that the eye is less sensitive to edges at oblique orientations than to those oriented horizontally or vertically, and a metric that incorporated that feature might perform better than the isotropic metrics we have implemented so far.

The ability to predict the visual impact of a given wave aberration is important for several reasons. First, this information can guide the clinician in selecting the best strategy for improving vision in each patient. For example, are the higher order aberrations in the patient's wave aberration severe enough to warrant customized refractive surgery, or is she likely to benefit just as much from conventional refractive surgery? If the patient is complaining of haloes, flares, monocular diplopia, or other visual defects, can the problem be linked to the eye's optical performance, is the patient unusually sensitive to small defects in vision, or are other neural factors implicated? Second, metrics to predict the subjective impact of the wave aberration can be incorporated into algorithms to compute the best vision correction given a particular wave aberration. Methods of vision correction such as contact lenses, spectacles, and refractive surgery generally correct fewer aberrations than can be measured with wavefront sensing technology. For example, spectacles can correct only five aberrations (defocus, two astigmatism aberrations, and two prismatic aberrations), whereas wavefront sensors can reliably measure dozens of aberrations in normal human eyes. The higher order aberrations can influence the values of defocus and astigmatism that provide the best subjective image quality. The development of metrics for subjective image quality that include the effects of higher order aberrations will allow us to optimize vision correction.

Metric formats will now be discussed. One would probably choose to convert metric values into scores that reflect population norms. For example, if the metric were transformed to a percentile, the clinician would know what fraction of the patient population has worse optics than the patient in question.

The metrics described in the preferred embodiment are univariate: only one number is used to characterize the blur produced by the eye's wave aberration. However, blur is not a unity perceptual experience. A multivariate scheme would more accurately describe the subjective effect of a given wave aberration. For example, our experience with different wave aberrations suggests that some of them reduce the overall contrast of the image, while keeping edges crisp. Others keep contrast high but sharp edges become fuzzy. Still other aberrations, especially odd-order aberrations like coma, produce asymmetry in images such as flaring away from the object in one direction. This suggests a tripartite metric with separate numbers for contrast, sharpness, and symmetry in the retinal image. Ultimately, psychophysical experiments could determine the importance of each of these subjective qualities in overall image quality. Therefore, while the preferred embodiment features a univariate sharpness metric, the present invention can be expanded to include multivariate metrics.

One of the fundamental difficulties in choosing an optimum metric is that the optimum metric is highly dependent on the visual task. For example, a task that requires detecting relatively large features in a low contrast environment would demand a quite different metric that detecting tiny features at very high contrast. The optimum metric will no doubt depend on a very large number of factors such as the visual task, pupil size, luminance, object distance, individual differences in neural systems. The optimum metric will also depend on how image quality is measured. It is well known that some patients prefer a "softer" image than others.

Metrics for subjective image quality might also need to incorporate the fact that neural processing is plastic, changing its performance depending on the wave aberration it currently sees the world through. There is a long history of research revealing this plasticity. Distortions in the visual field, introduced with prisms, disappear with time, as do the chromatic fringes caused by chromatic aberration. Recent experiments by Pablo Artal, working with the present inventor, reveal that this plasticity extends to the monochromatic aberrations of the eye as well. Artal used the Rochester Adaptive Optic Ophthalmoscope to remove the wave aberration from a subject. He then replaced the wave aberration, either in its original orientation or rotated by some amount. Despite the fact that the rotation only changes the orientation of the aberrations and not the objective amount of retinal blur, the subjective blur changed dramatically. Subjects viewing the world through their own wave aberration reported that it was much sharper than when the wave aberration was rotated. These observations support clinical wisdom that patients will often reject astigmatic corrections that improve image quality, but cause too large a departure from their normal experience of the world. The effect has far-reaching implications for vision correction, since it means that subjects who receive an aberration-free view of the world through customized correction may require time to adjust to the benefit. Alternatively, vision correction might best be accomplished through a multiple step process that ultimately converges on the desired correction.

The development and validation of a metric based on the average patient is the first goal. But this metric could be customized depending on the specific characteristics of each patient. For example, older patients are likely to have more light scatter, their pupil sizes are smaller on average, their accommodation range is reduced, and they will probably tolerate large changes in vision correction less readily. A metric that included patient age as a parameter would help to ensure the optimum vision correction. The optimum metric for someone with a poor neural contrast sensitivity will be different than the metric for someone with exquisite neural sensitivity. It may ultimately be possible to build known features of an individual patient's nervous system into the metric. For example, with laser interferometry or adaptive optics, it is possible to measure the neural performance of the eye independent of its optical quality. There are large variations in the neural performance of different eyes, even normal eyes, and the metric could be customized to each patient accordingly. One could also customize the metric based on lifestyle. Patients with reduced accommodation or whose lifestyle required good focus over a large range of viewing distances might benefit from a increase in spherical aberration compared with a patient, such as a pilot, who would prefer to optimize performance at infinity.

The metric according to the present claimed invention allows fully automated refraction. Autorefractors have not replaced subjective refraction as the ultimate method to prescribe vision correction. The advent of the wave front sensing reopens the possibility of fully-automated refraction. Wave front sensors provide much more information than autorefractors, since they indicate the fate of light as it passes through every point in the pupil. A fast algorithm has been described to compute the optimum vision correction for any metric from wave aberration data. Coupled with a biologically-plausible metric designed to mimic the eye and brain of each patient, wave front sensors may ultimately surpass the clinical refraction as the preferred method for choosing the best correction, whether for refractive surgery, spectacles, contact lenses, or intraocular lenses.

The sharpness metric will have utility in describing the quality of vision to patients, which goes beyond a descriptor such as "20/20" vision. The metric can expected be extended to indicate where a patient's vision fits within the general population. Such information would be useful in guiding choices about refractive surgery, contact lens or spectacles.

Four levels of use for a sharpness metric are contemplated:

1. A sharpness metric, for research and clinical use, for communicating the quality of vision in a simple single parameter;

2. An automated process for computing the sharpness metric, for clinical use in communicating with patients, built, as a feature, into any wavefront measuring device, including standalone diagnostic devices and those devices used as part of an integrated refractive surgery system;

3. Use of the sharpness metric as an optimization parameter in algorithms to calculate the optimal prescription for improved vision correction in customized refractive surgery; and 4. Use of the sharpness metric as an optimization parameter in algorithms to calculate the optimal prescription for vision correction for spectacles, contact lenses, and intraocular lenses of any kind, from a new class of auto-refractor and phoropter devices, which incorporate wave front sensing.

Two experiments have been designed to compare the effectiveness of different metrics in determining the subjective impact of the wave aberration. In both experiments, subjects viewed a visual stimulus through a deformable mirror in an adaptive optics system that compensates for the subject's wave aberration. In the first experiment, the subject's wave aberration was replaced by the wave aberration corresponding to an individual Zernike mode. The subject then adjusted the coefficient of the Zernike mode to match the blur of a standard stimulus. In the second experiment, the subject viewed the stimulus with the wave aberration of one of 59 Lasik patients post-op and matched the blur by adjusting defocus.

The invention will be disclosed in terms of integration. However, data are normally taken pixel by pixel, so that discrete summation is used instead. Therefore, throughout the specification and claims, the word "integration" will be understood to encompass discrete summation as well.

BRIEF DESCRIPTION OF THE DRAWINGS

A preferred embodiment of the present invention will be set forth in detail with reference to the drawings, in which:

FIG. 7 shows the varying effectiveness of Zernike modes;

DETAILED DESCRIPTION OF THE PREFERRED EMBODIMENT

A preferred embodiment of the present invention will be set forth in detail with reference to the drawings.

In the preferred embodiment, the sharpness metric S is calculated from the point spread function (PSF) and a neural point spread function based on psychophysical experiments. The sharpness metric S has the form $$S = \max(PSF(x,y) \circledast \exp[-(x^2+y^2)/\sigma^2]).$$

The optical PSF is convolved with the neural PSF, where the latter is expressed as a Gaussian. The maximum value of this convolution is the metric value.

As shown above, the neural PSF is represented by a Gaussian function. The value of σ which best fits the data is approximately 0.8 minute of arc for the first experiment, though a somewhat large value is prefered in the second experiment. This parameter could be adjusted depending on the quality of the patient's neural visual system.

Figure 1:
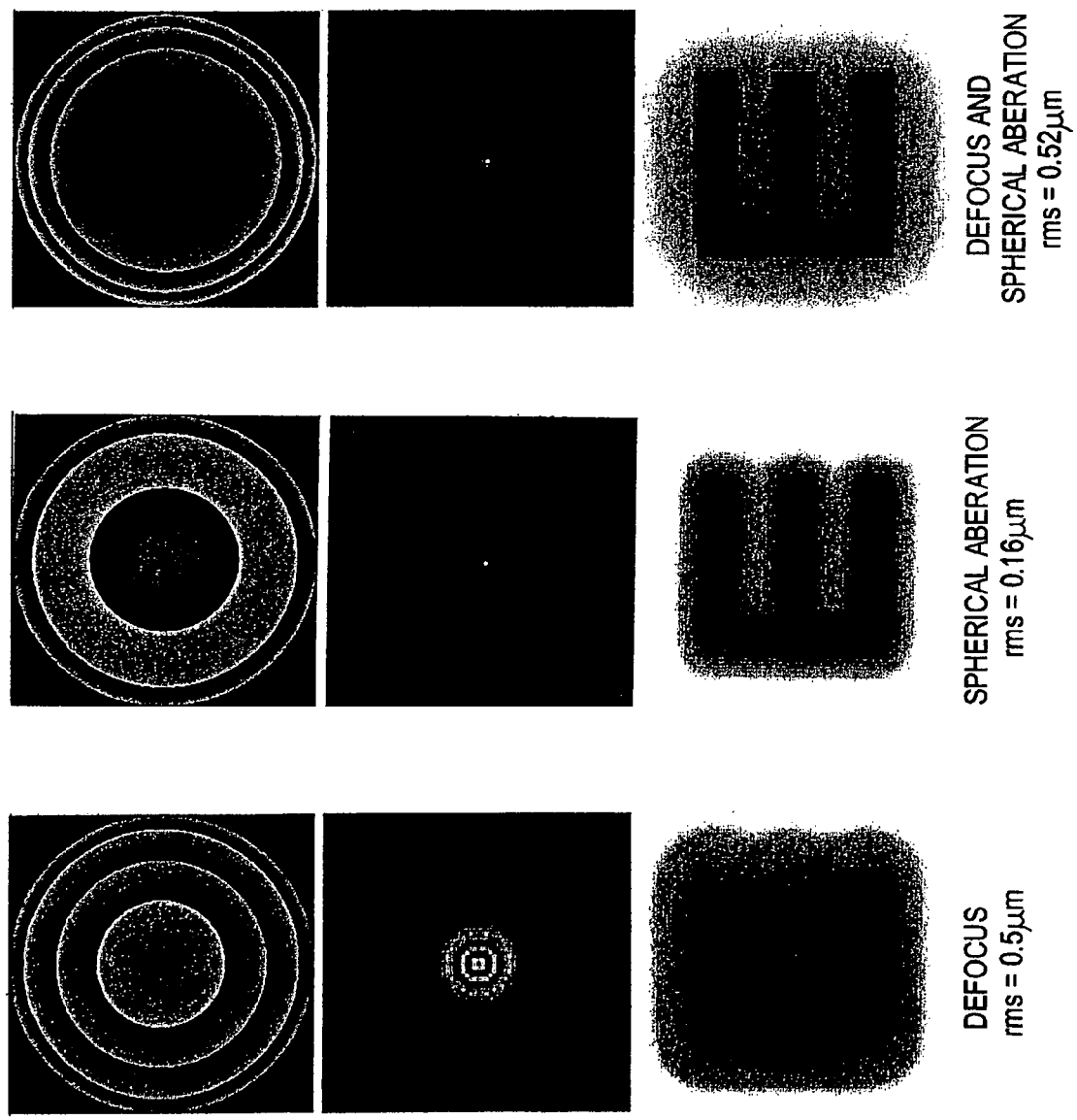
FIG. 1 shows the effects of combinations of various Zernike modes.
Figure 2:
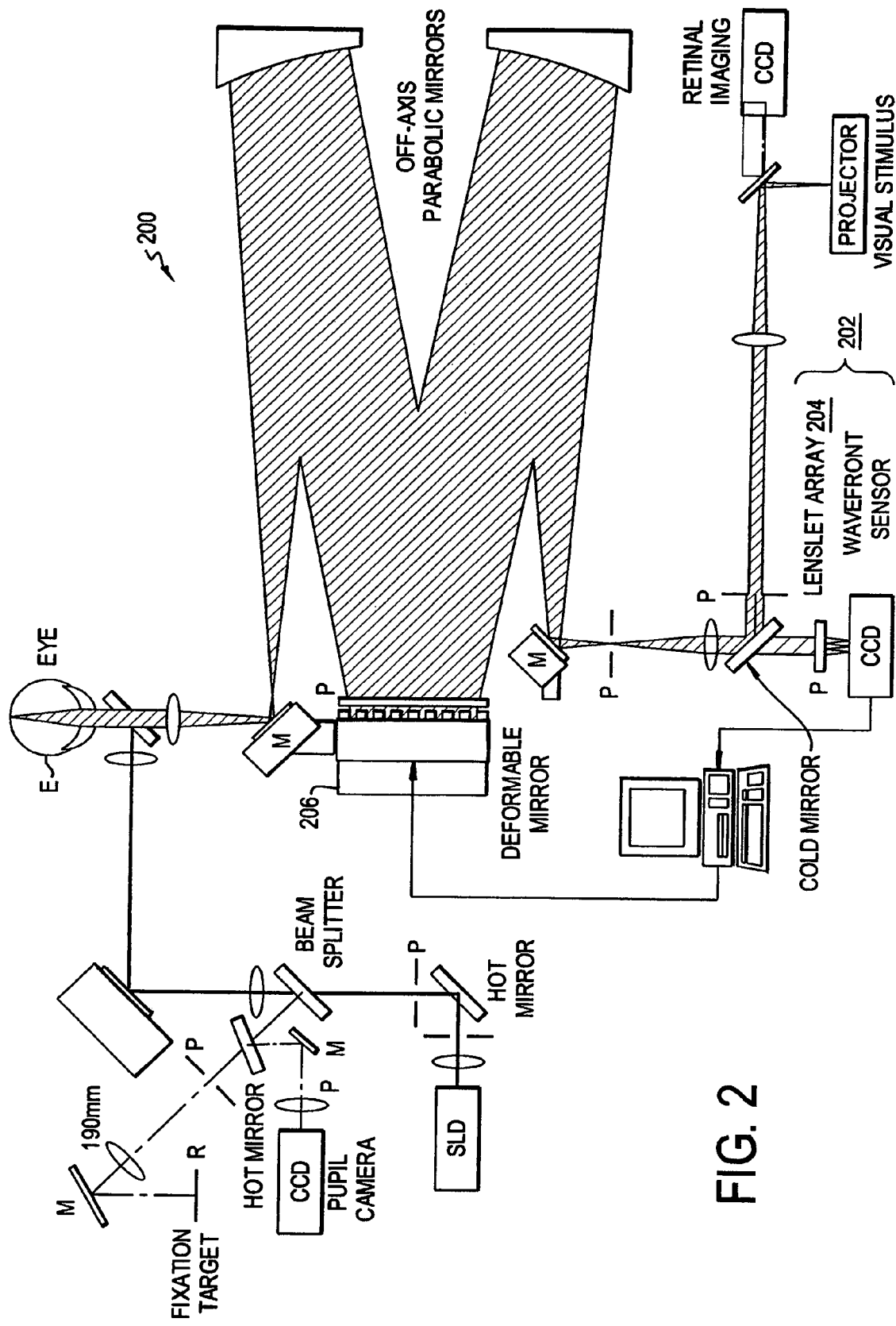
FIG. 2 shows an experimental setup used to test the sharpness metric of the preferred embodiment.

FIG. 2 shows the setup of the adaptive optics system 200 for the matching experiment. In FIG. 2, the letters R, M and P indicate conjugate planes. This adaptive optics system 200 uses a Hartmann-Shack wavefront sensor 202, conjugate with the pupil plane of the subject's eye E, to make measurements of the eye's wave aberrations at 30 Hz. This Hartmann-Shack wave-front sensor 202 has 177 lenslets (not individually shown) in a square array 204, which can measure the aberrations for a 6 mm pupil up to tenth radial order, corresponding to 63 Zernike modes. The wave aberration measurements were made at 810 nm wavelength. A deformable mirror 206 with 97 PMN actuators (not individually shown), also conjugate with the subject's pupil plane, is used to correct the subject's wave aberrations based on the measurements from the Hartmann-Shack wavefront sensor 202. In this experiment, besides removing the higher order aberrations in the eye on each trial, the deformable mirror also acted as an aberration generator to blur the subject's vision either with individual Zernike modes or with the wave aberrations of Lasik patients.

Measurements were on the right eyes of 6 subjects respectively. During the measurement, the subject's head was stabilized with a bite bar, and the subject's pupil was dilated with cyclopentolate hydrochloride (2.5%).

Figure 3A:
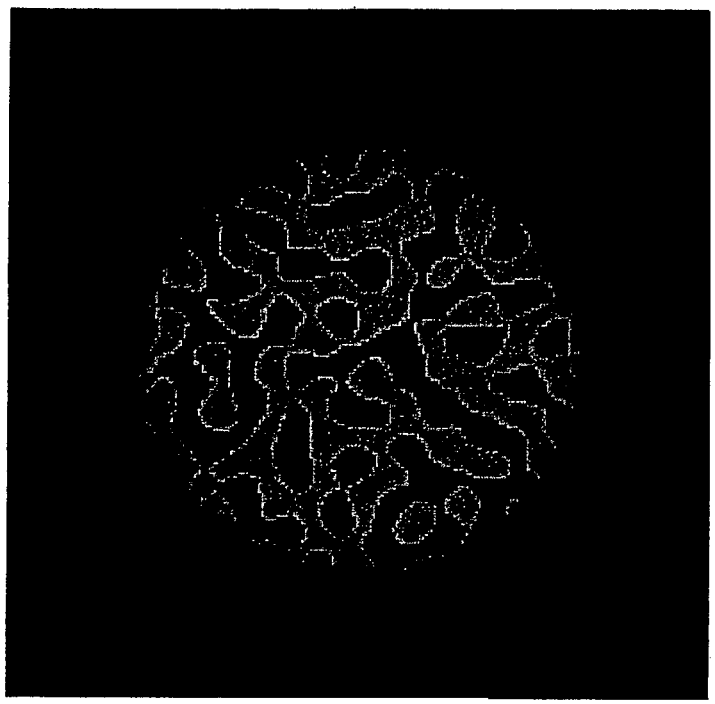
FIGS. 3A–3E show mode blur matching.

Subjects viewed a binary noise stimulus through adaptive optics system. The stimulus used in the matching experiment, shown in FIG. 3A, contains sharp edges at all orientations. On each trial, the stimulus pattern was generated randomly by computer. The subject viewed the stimulus for 500 ms immediately after the deformable mirror generated the standard aberrations or the tested aberration. At other times, the subject viewed a uniform field. The artificial pupil diameter was 6 mm, and the test field subtended 1 degree visual, angle. A Gaussian function smoothed the edge of the field. The stimulus was viewed in 550 nm monochromatic light.

Figure 3B:
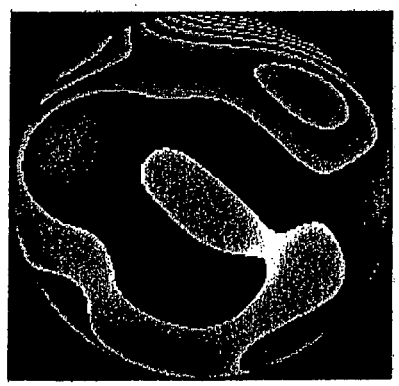
Figure 3C:
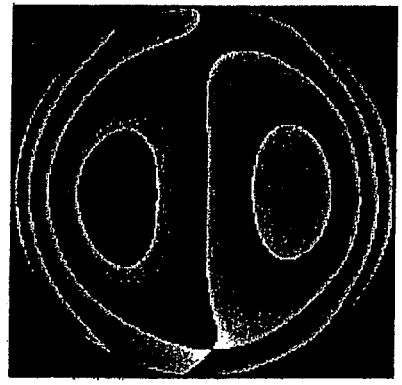
Figure 3D:
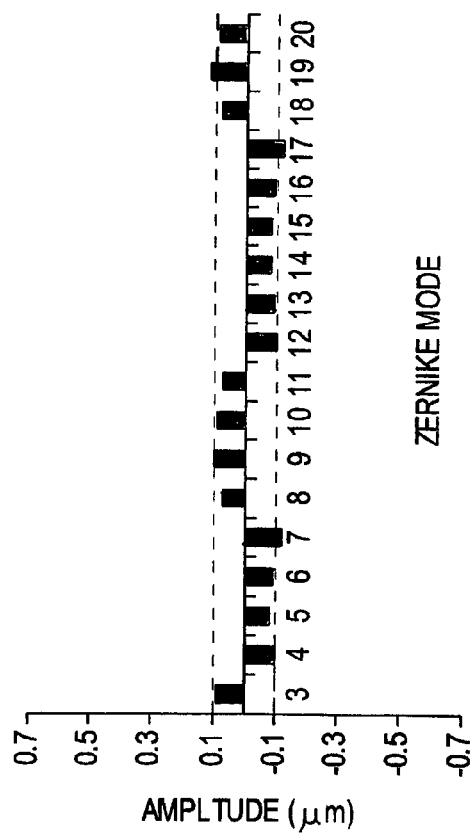
Figure 3E:
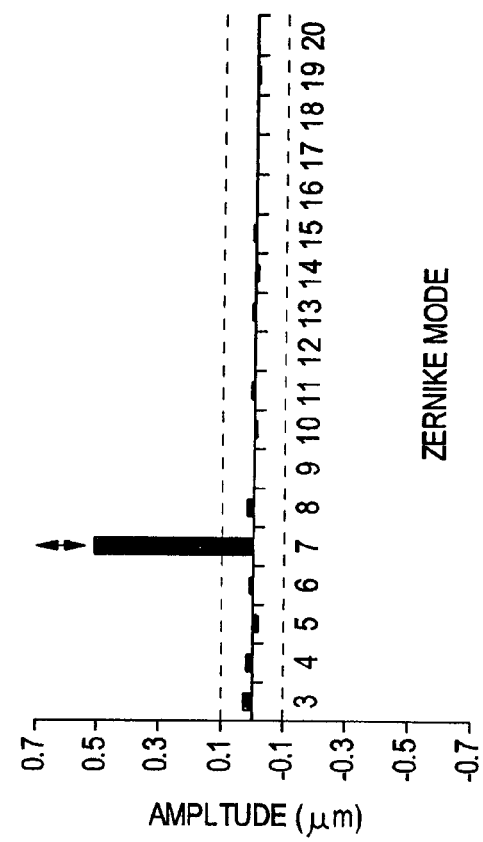
Figure 4D:
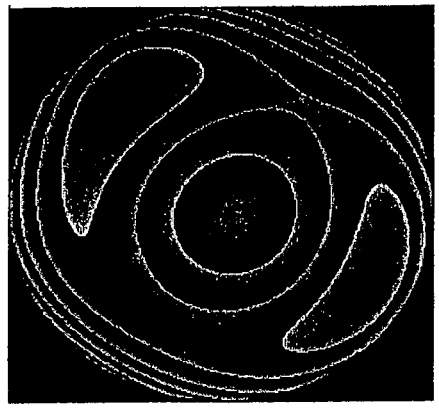
FIGS. 4A–4D show wave aberrations from a Lasik post-operative patient.
Figure 4H:
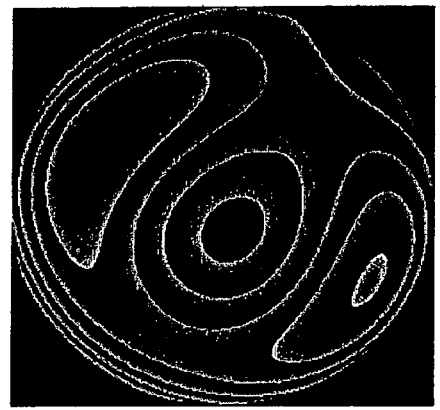
FIGS. 4E–4H show wave aberrations caused by corrective optics.
Figure 4C:
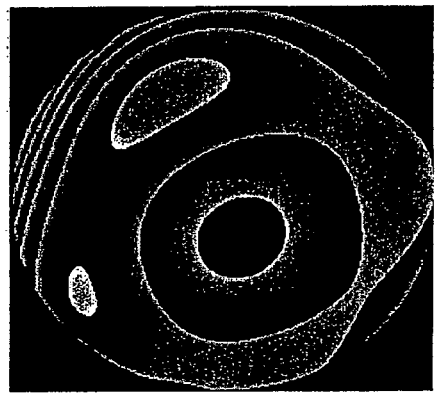
Figure 4G:
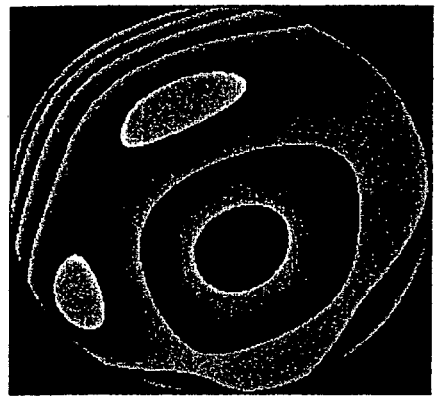
Figure 4B:
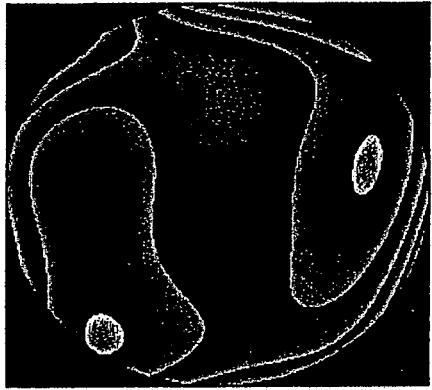
Figure 4F:
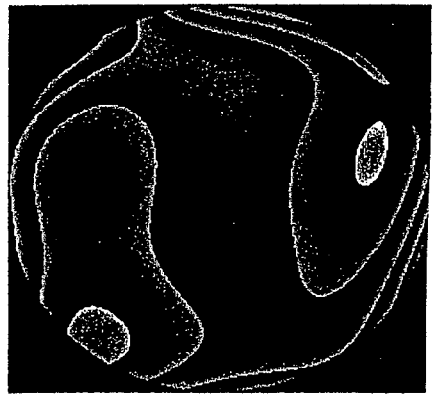
Figure 4A:
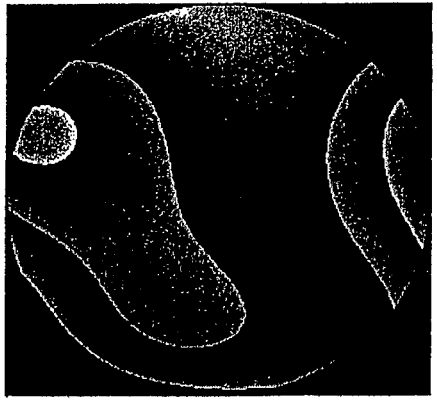
Figure 4E:
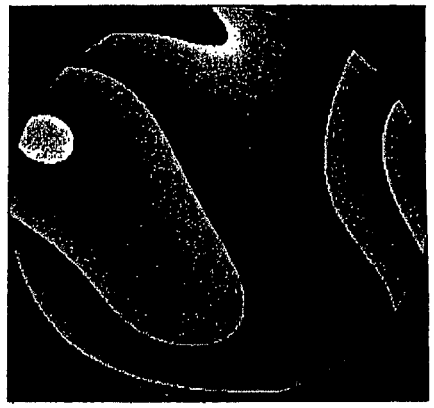
Figure 5A:
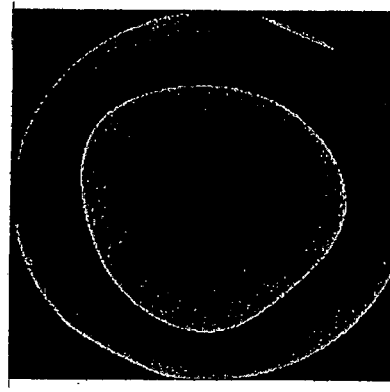
FIGS. 5A–5D show blur matching of patient wave aberrations.
Figure 5B:
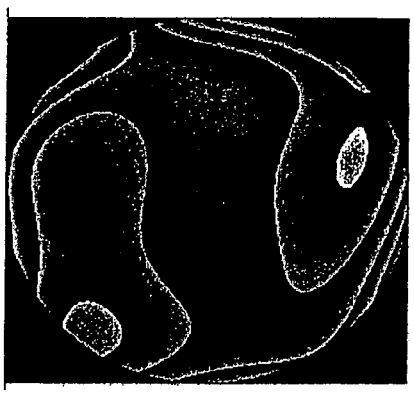
Figure 5C:
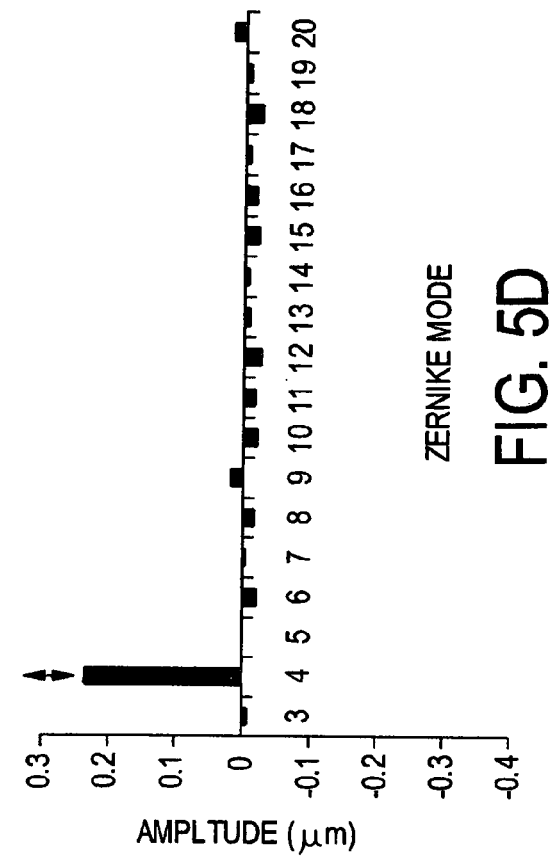
Figure 5D:
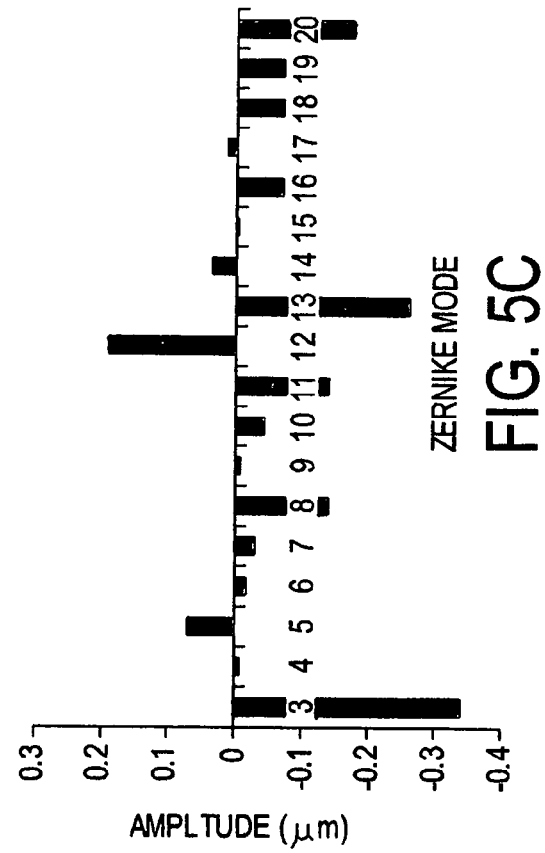

In the psychophysical measurement of the subjective blur of individual Zernike modes, the adaptive optics system blurred the subject's vision with a standard aberration or a single Zernike mode alternating in time. The standard aberration was created by combining all 18 Zernike modes from 2nd through 5th order with 0.1 μm absolute value for each mode. The test aberration was only one single Zernike mode whose coefficient could be adjusted by the subject to produce the same subjective blur in the stimulus as the standard aberration. FIGS. 3B and 3C show, respectively, the standard aberration and one of the test aberrations generated with adaptive optics in one subject's eye. The corresponding Zernike modes are shown in FIGS. 3D and 3E. Each mode has two matching values, one positive and one negative. The matching measurement for each mode was performed 8 times, 4 times to match the positive value and 4 times to match the negative value. The matching value of one mode to the standard aberration is the average from the absolute values of these 8 matches.

A similar matching procedure was used to measure the subjective blur produced by patient wave aberrations. The key differences were that the standard aberration was replaced by one of 59 wave aberrations from post-op Lasik patients, and defocus was used as the aberration for the blur matching. Each patient aberration, containing 18 Zernike modes, was measured with a wavefront sensor. The defocus of each patient's wave aberration was set to zero in the standard aberration. For each match, the adaptive optics system replaced the subject's wave aberration with that of one of the patients. FIGS. 4A–4D show a sample of patient aberrations, while corresponding FIGS. 4E–4H show the same aberration generated in the eye of one of the subjects with adaptive optics.

FIGS. 5A–5D show the matching procedure in which the subject changed the value of defocus to match the blur caused by the patient aberration. The stimulus is the same as that shown in FIG. 3A. FIGS. 5A–5D show, respectively, the patient wave aberration, defocus, the Zernike modes corresponding to the patient wave aberration, and the Zernike modes corresponding to defocus. The reason we chose defocus as the test aberration to quantify the blur caused by the patient wave aberration is that defocus, expressed in diopters is familiar. The matching value of defocus to each patient's aberration was measured 4 times at the positive value and 4 times at negative value. The matching value was the average from the absolute of values of these 8 measurements.

Figure 6:
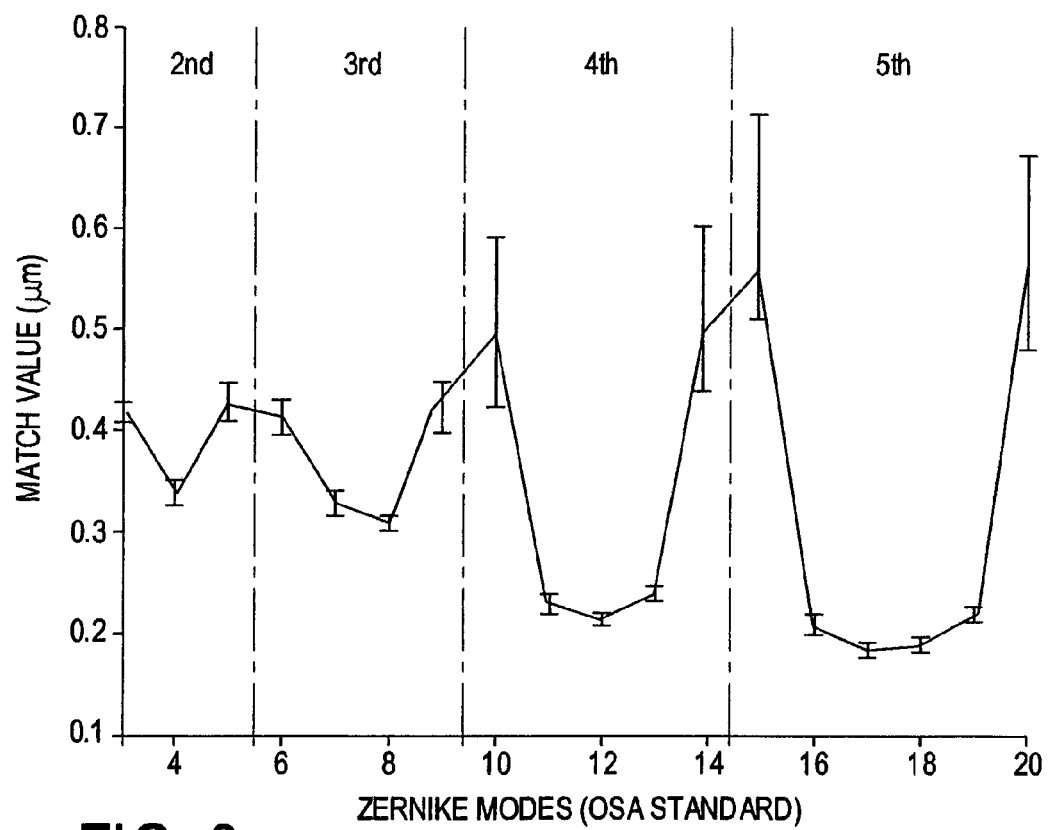
FIG. 6 shows the differences among aberrations in their ability to blur.
Figure 8:
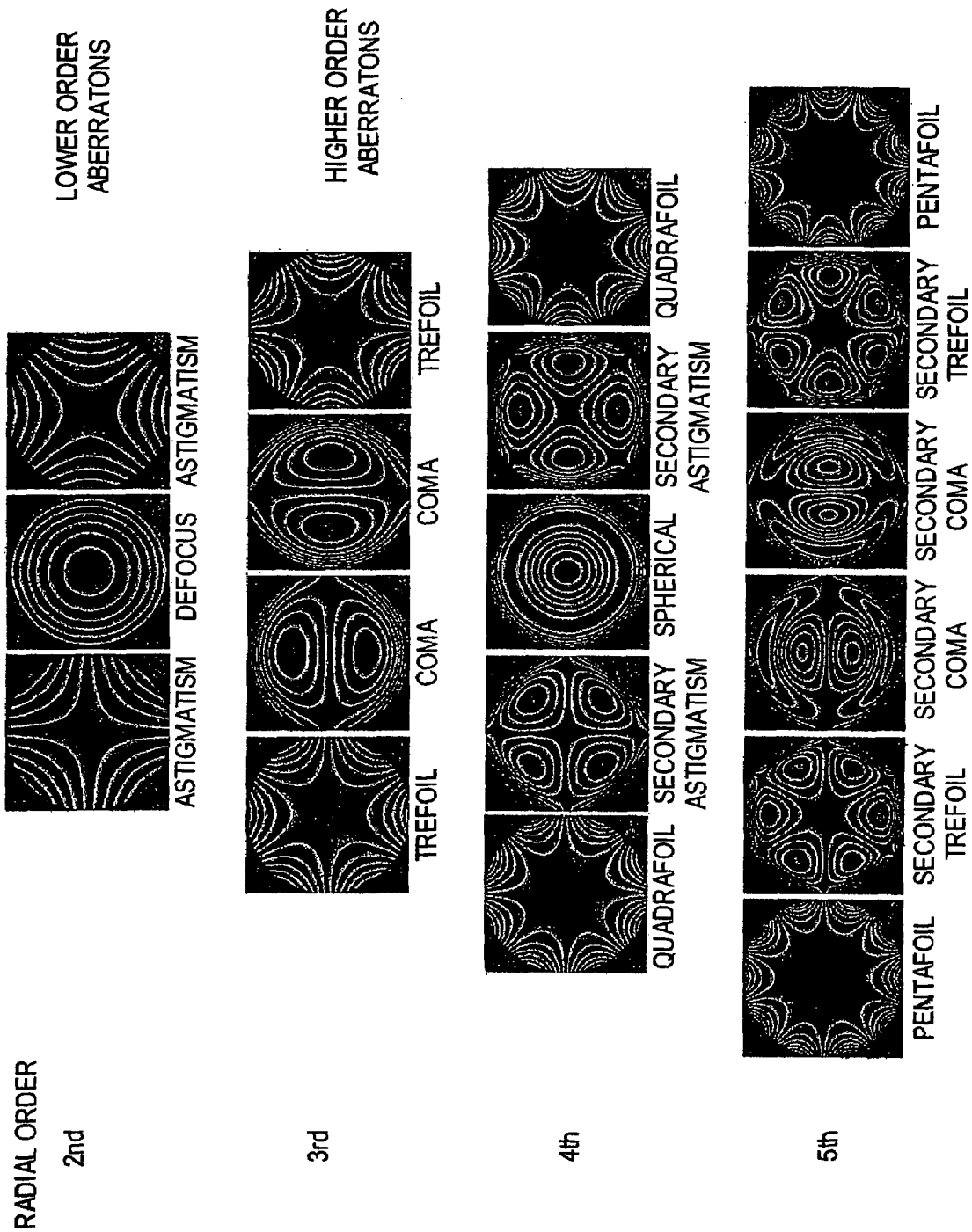
FIG. 8 shows the various Zernike modes.

FIG. 6 shows the matching results for individual Zernike modes. The lower the matching value, the stronger the aberration. Aberrations in the center of each order are stronger than those at the edge. This agrees with the simulation in FIG. 7 showing that equal amplitudes of RMS produce large differences in subjective blur. Note that the letters at the center of the pyramid are more blurred than those along the flanks. One can see in FIG. 8 that the wave aberrations along the flanks have relatively large regions where the wavefront is flat, unlike those in the center of the pyramid.

Figure 9B:
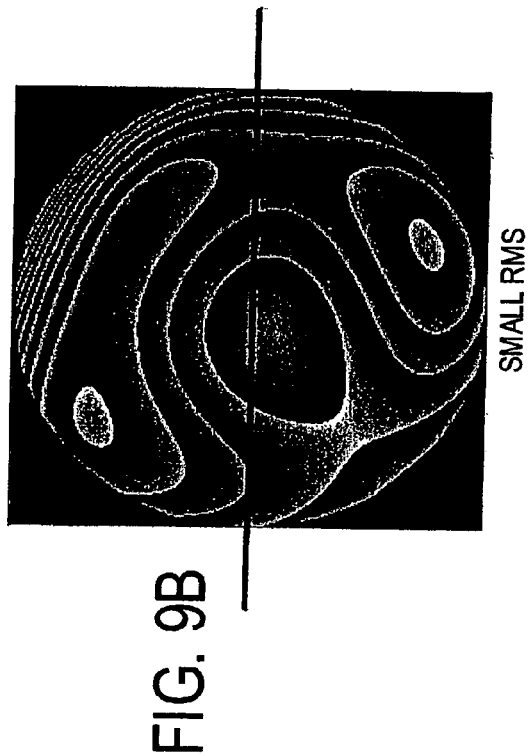
FIGS. 9A–9C show the effects of wave aberration RMS.
Figure 9A:
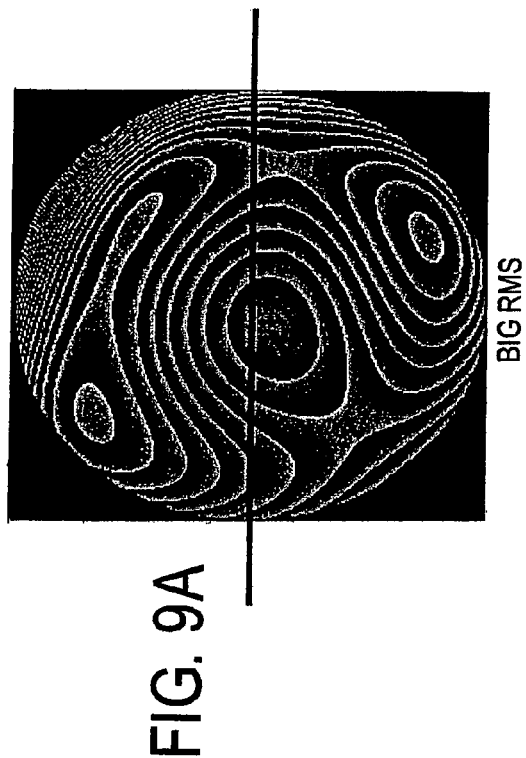
Figure 9C:
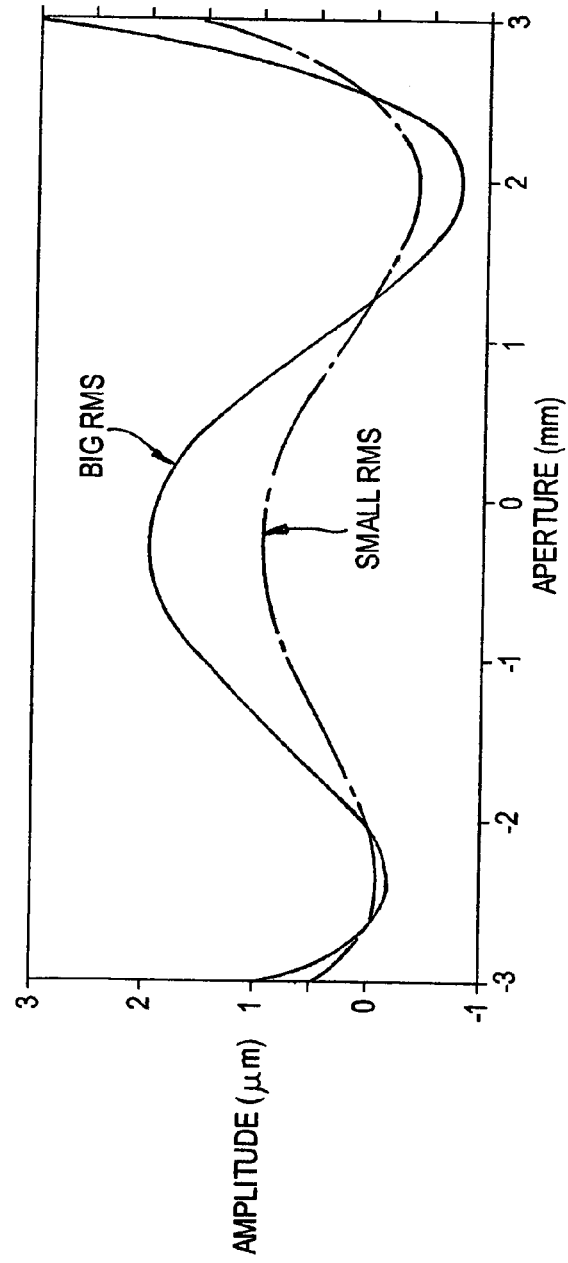
Figure 10:
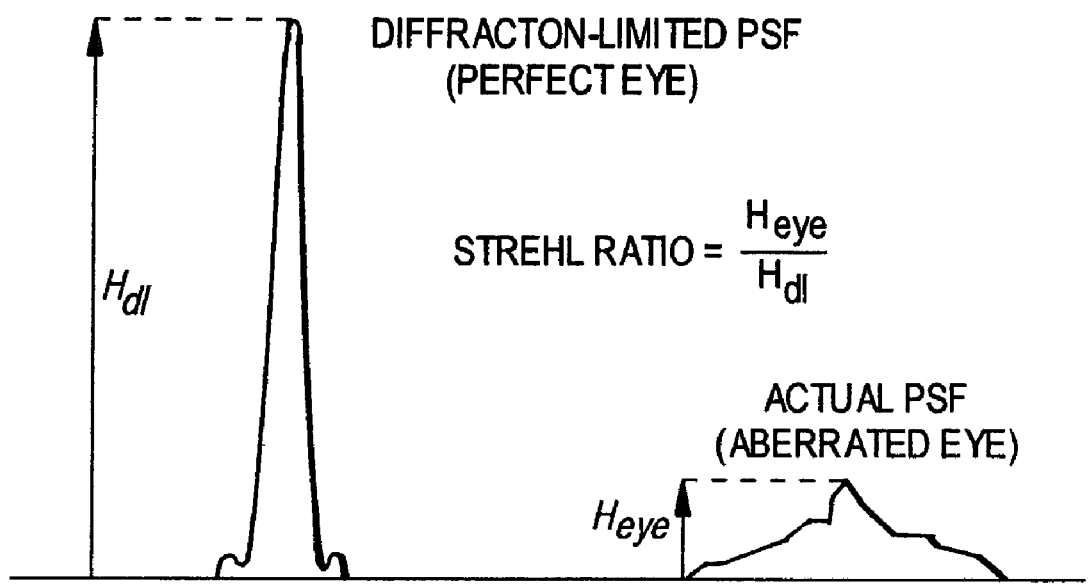
FIG. 10 shows the derivation of the Strehl ratio.
Figure 11:
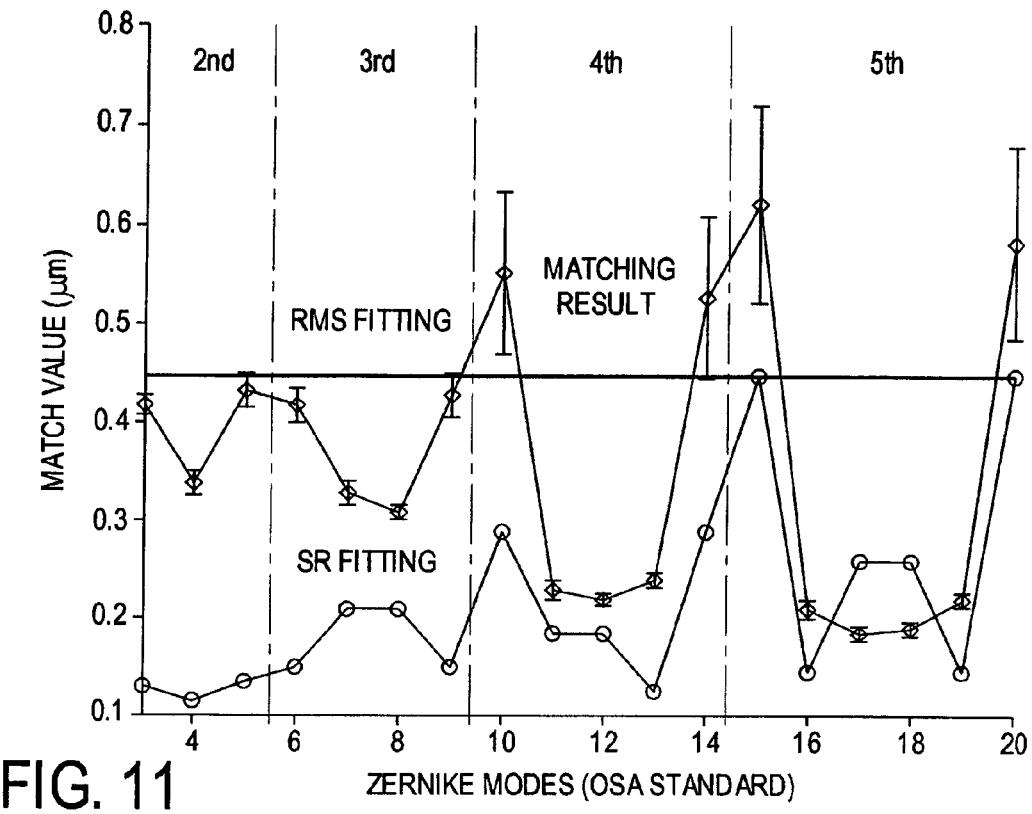
FIG. 11 shows the deficiencies of RMS and the Strehl ratio in predicting subjective sharpness.
Figure 12:
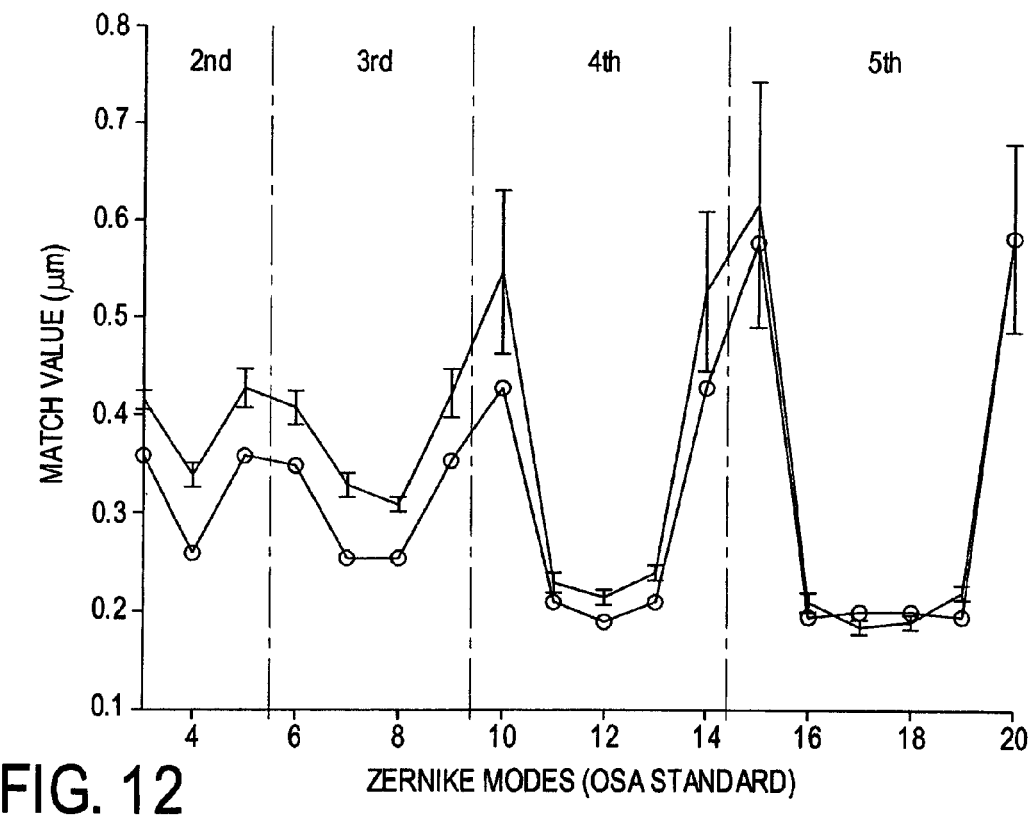
FIG. 12 shows the predictive value of the sharpness metric.

FIGS. 9A–9C and 10 define two commonly used metrics, RMS wavefront error and Strehl ratio. Mathematically, RMS can be expressed as $RMS=\sqrt{\Sigma(\phi(x,y)-mean)^2}$. The Strehl ratio is the ratio of the point spread function of the aberrated eye to the point spread function of a perfect eye, that is, the diffraction-limited point spread function. FIGS. 9A and 9B show cases for a large RMS and a small RMS, respectively, while FIG. 9C shows a plot of amplitude as a function of aperture. FIG. 11 shows that neither of these metrics does a good job of predicting the matching data. This leads us to create a new sharpness metric. FIG. 12 is the result using sharpness metric to predict the matching data. Compared with fitting results from RMS wavefront error and Strehl ratio metrics, the neural sharpness metric is much more effective at describing the subjective sharpness of images viewed with the wave aberrations of real eyes.

Figure 13C:
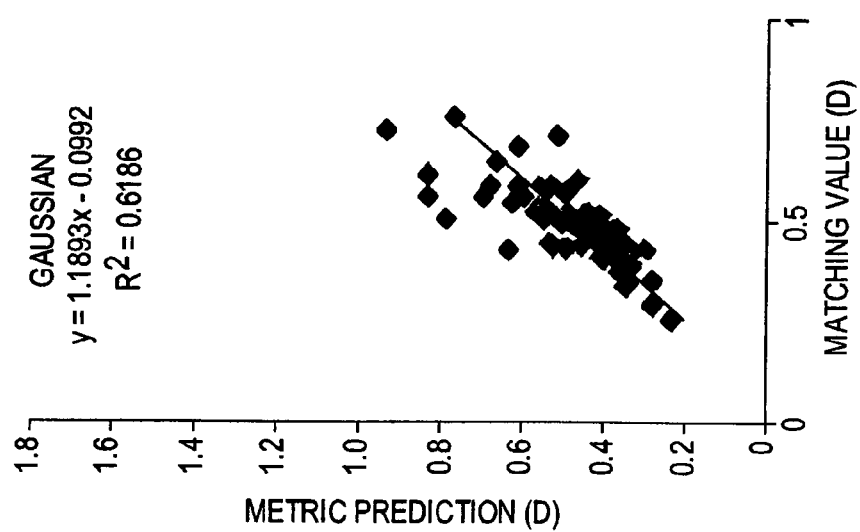
FIGS. 13A–13C show the various predictive abilities of the RMS, the Strehl ratio, and the sharpness metric, respectively.
Figure 13B:
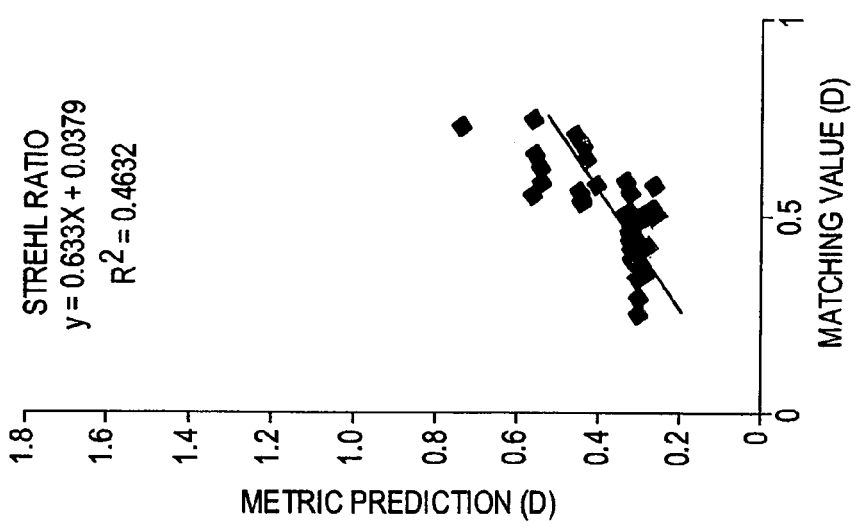
Figure 13A:
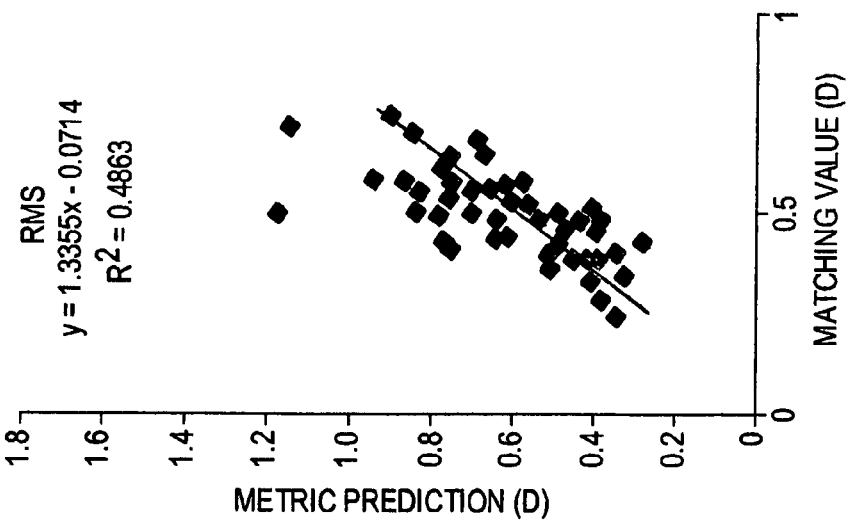

We also used RMS, the Strehl ratio and neural sharpness metric to fit the matching results from 6 subjects for the subjective blur of real aberrations from 59 post-op Lasik patients. FIGS. 13A–13C show the correlation between matching value and prediction data from the metrics. The sharpness metric did the best at predicting the image quality of the patient's aberrations.

Figure 14:
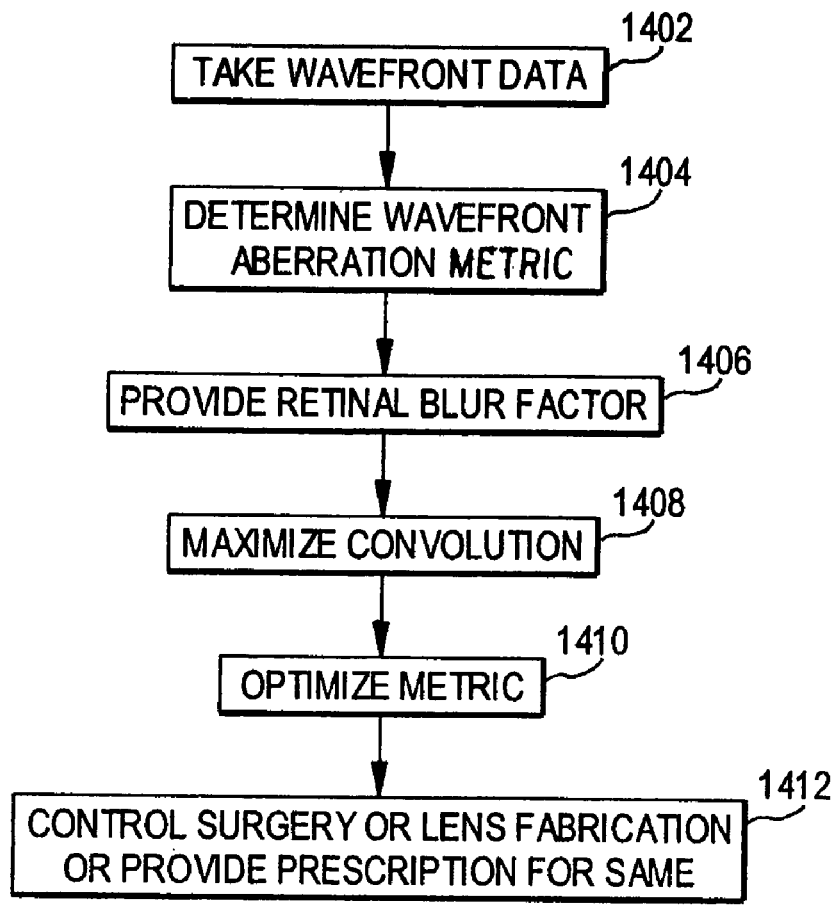
FIG. 14 shows a flow chart of a process for correcting vision by use of the sharpness metric.

Various uses for the new metric will be discussed with reference to FIGS. 14 and 15. The new metric can be implemented as an improvement to the method and apparatus of U.S. Pat. No. 5,777,719, which names the present inventor as a co-inventor.

Figure 15:
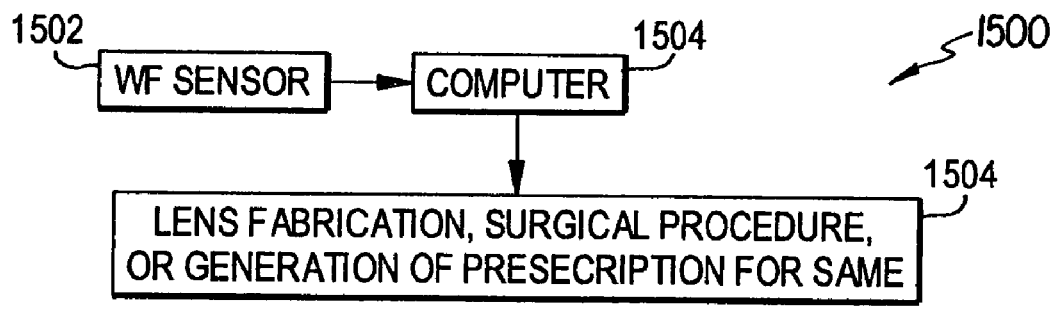
FIG. 15 shows a schematic diagram of an apparatus for correcting vision by use of the sharpness metric.

In a system 1500 as shown in FIG. 15, a wavefront sensor 1502 is in communication with, or has integrated into it, a computer 1504. The wavefront sensor 1502 and the computer 1504 perform the following steps shown in FIG. 14: taking the wavefront data, step 1402; determining the wavefront aberration metric, step 1404; providing the neural PSF, step 1406; forming a the maximum of the convolution of the two to form the sharpness metric, step 1408; and determining an optimization of that metric, step 1410. The result of the optimization can then be used to control surgery on the eye or the fabrication of a lens (e.g., spectacle, contact, or intraocular) or to generate a prescription for surgery or corrective lenses (FIG. 14, step 1412; FIG. 15, component 1506). The steps can be automated.

Yet another example of the utility of the metric is in retinal imaging. The optimization of the metric can be used to control a deformable mirror or other adaptive optical element, as taught in the above-cited U.S. Pat. No. 5,777,719, to improve the image of the retina. This would be valuable if, for example, the correction element were incapable of correcting all the aberrations that could be measured with the wavefront sensor.

While a preferred embodiment of the present invention has been set forth above, those skilled in the art who have reviewed the present disclosure will readily appreciate that other embodiments can be realized within the scope of the present invention. For example, other metrics representing wavefront aberration can be used, as can other factors representing the patient's response. Therefore, the present invention should be construed as limited only by the appended claims.

I claim:

1. A method for determining a subjective sharpness of vision of a subject, the method comprising:
    (a) taking wavefront aberration data from an eye of the subject, the wavefront aberration data representing a wavefront aberration which affects the subjective sharpness;
    (b) from the wavefront aberration data, determining a retinal image quality function which represents an effect of the wavefront aberration on the sharpness;
    (c) providing a neural quality function which represents the effect of the subject's neural processing on the sharpness; and
    (d) from the retinal image quality function and the neural quality function, deriving a subjective sharpness metric which represents the subjective sharpness wherein step (d) comprises convolving the retinal image quality function by the neural quality function to form a product to form a convolution, and wherein step (d) further comprises computing a maximum value of the convolution over a retinal plane of the living eye.

2. The method of claim 1, wherein the retinal image quality function is a point spread function.

3. The method of claim 2, wherein the neural quality function is a Gaussian function of spatial coordinates in the retinal plane.

4. A method for determining a subjective sharpness of vision of a subject, the method comprising:
    (a) taking wavefront aberration data from an eve of the subject, the wavefront aberration data representing a wavefront aberration which affects the subjective sharpness;
    (b) from the wavefront aberration data, determining a retinal image quality function which represents an effect of the wavefront aberration on the sharpness;
    (c) providing a neural quality function which represents the effect of the subject's neural processing on the sharpness; and
    (d) from the retinal image quality function and the neural quality function, deriving a subjective sharpness metric which represents the subjective sharpness, wherein the neural quality function represents a response of the subject's retina and brain, and wherein the neural quality function further represents a variation in sensitivity of the eye to edges at horizontal, vertical and oblique orientations.

5. A method for determining a subjective sharpness of vision of a subject, the method comprising:
    (a) taking wavefront aberration data from an eye of the subject, the wavefront aberration data representing a wavefront aberration which affects the subjective sharpness;
    (b) from the wavefront aberration data, determining a retinal image quality function which represents an effect of the wavefront aberration on the sharpness;
    (c) providing a neural quality function which represents the effect of the subject's neural processing on the sharpness; and
    (d) from the retinal image quality function and the neural quality function, deriving a subjective sharpness metric which represents the subjective sharpness, wherein the subjective sharpness metric is multivariate.

6. A method for determining an optimal correction for vision of a subject, the method comprising:
    (a) taking wavefront aberration data from an eve of the subject, the wavefront aberration data representing a wavefront aberration which affects the subjective sharpness;
    (b) from the wavefront aberration data, determining a retinal image quality function which represents an effect of the wavefront aberration on the sharpness;
    (c) providing a neural quality function which represents an effect of the subject's neural processing on the sharpness;
    (d) from the retinal image quality function and the neural quality function, deriving a subjective sharpness metric which represents the subjective sharpness; and
    (e) determining a correction for the vision which optimizes the sharpness metric, wherein step (d) comprises convolving the retinal image quality function by the neural quality function to form a convolution, and wherein step (d) further comprises computing a maximum value of the convolution over a retinal plane of the living eye.

7. The method of claim 6, wherein the retinal image quality function is a point spread function.

8. The method of claim 7, wherein the neural quality function is a Gaussian function of spatial coordinates in the retinal plane.

9. A method for determining an optimal correction for vision of a subject, the method comprising:
    (a) taking wavefront aberration data from an eye of the subject, the wavefront aberration data representing a wavefront aberration which affects the subjective sharpness;
    (b) from the wavefront aberration data, determining a retinal image quality function which represents an effect of the wavefront aberration on the sharpness;
    (c) providing a neural quality function which represents an effect of the subject's neural processing on the sharpness;
    (d) from the retinal image quality function and the neural quality function, deriving a subjective sharpness metric which represents the subjective sharpness; and
    (e) determining a correction for the vision which optimizes the sharpness metric, wherein the neural quality function represents a response of the subject's retina and brain, and wherein the neural quality function further represents a variation in sensitivity of the eye to edges at horizontal, vertical and oblique orientations.

10. A method for determining an optimal correction for vision of a subject, the method comprising:
(a) taking wavefront aberration data from an eye of the subject, the wavefront aberration data representing a wavefront aberration which affects the subjective sharpness;
(b) from the wavefront aberration data, determining a retinal image quality function which represents an effect of the wavefront aberration on the sharpness;
(c) providing a neural quality function which represents an effect of the subject's neural processing on the sharpness;
(d) from the retinal image quality function and the neural quality function, deriving a subjective sharpness metric which represents the subjective sharpness; and
(e) determining a correction for the vision which optimizes the sharpness metric, wherein the subjective sharpness metric is multivariate.

11. An apparatus for determining a subjective sharpness of vision of a subject, the apparatus comprising:
a wavefront sensor for taking wavefront aberration data from an eye of the subject, the wavefront aberration data representing a wavefront aberration which affects the subjective sharpness; and
a computing device, in communication with or integrated into the wavefront sensor, for:
(i) determining, from the wavefront aberration data, a retinal image quality function which represents an effect of the wavefront aberration on sharpness;
(ii) providing a neural quality function which represents an effect of neural processing of the subject on sharpness; and
(iii) from the retinal image quality function and the neural quality function, deriving a subjective sharpness metric which represents the subjective sharpness, wherein the computing device performs step (iii) by convolving the retinal image quality function by the neural quality function to form a convolution, and wherein the computing device performs step (iii) further by computing a maximum of the convolution over a retinal plane of the living eye.

12. The apparatus of claim 11, wherein the retinal image quality function is a point spread function.

13. The apparatus of claim 12, wherein the neural quality function is a Gaussian function of spatial coordinates in the retinal plane.

14. An apparatus for determining a subjective sharpness of vision of a subject, the apparatus comprising:
a wavefront sensor for taking wavefront aberration data from an eye of the subject, the wavefront aberration data representing a wavefront aberration which affects the subjective sharpness; and
a computing device, in communication with or integrated into the wavefront sensor, for:
(i) determining, from the wavefront aberration data, a retinal image quality function which represents an effect of the wavefront aberration on sharpness;
(ii) providing a neural quality function which represents an effect of neural processing of the subject on sharpness; and
(iii) from the retinal image quality function and the neural quality function, deriving a subjective sharpness metric which represents the subjective sharpness, wherein the computing device performs step (iii) by convolving the retinal image quality function by the neural quality function to form a convolution, wherein the computing device performs step (iii) by convolving the retinal image quality function by the neural quality function to form a convolution, wherein the computing device performs step (iii) further by computing a maximum of the convolution over a retinal plane of the living eye.

15. An apparatus for determining a subjective sharpness of vision of a subject, the apparatus comprising:
a wavefront sensor for taking wavefront aberration data from an eye of the subject, the wavefront aberration data representing a wavefront aberration which affects the subjective sharpness; and
a computing device, in communication with or integrated into the wavefront sensor, for:
(i) determining, from the wavefront aberration data, a retinal image quality function which represents an effect of the wavefront aberration on sharpness;
(ii) providing a neural quality function which represents an effect of neural processing of the subject on sharpness; and
(iii) from the retinal image qiuality function and the neural qiuality function, deriving a subjective sharpness metric which represents the subjective sharpness, wherein the computing device performs step (iii) by convolving the retinal image quality function by the neural quality function to form a convolution, wherein the subjective sharpness metric is multivariate.

16. An apparatus for determining an optimal correction for vision of a subject, the apparatus comprising:
a wavefront sensor for taking wavefront aberration data from an eye of the subject, the wavefront aberration data representing a wavefront aberration which affects the subjective sharpness; and
a computing device, in communication with or integrated into the wavefront sensor, for:
(i) determining, from the wavefront aberration data, a retinal image quality function which represents an effect of the wavefront aberration on the sharpness;
(ii) providing a neural quality function which represents an effect of neural processing of the subject on the sharpness;
(iii) from the retinal image quality function and the neural quality function, deriving a subjective sharpness metric which represents the subjective sharpness; and
(iv) determining a correction for the vision which optimizes the sharpness metric, wherein the computing device performs step (iii) by convolving the retinal image quality function by the neural quality function to form a convolution, and wherein the computing device performs step (iii) further by computing a maximum of the convolution over a retinal plane of the living eye.

17. The apparatus of claim 16, wherein the retinal image quality function is a point spread function.

18. The apparatus of claim 17, wherein the neural quality function is a Gaussian function of spatial coordinates in the retinal plane.

19. An apparatus for determining an optimal correction for vision of a subject, the apparatus comprising:
a wavefront sensor for taking wavefront aberration data from an eye of the subject, the wavefront aberration data representing a wavefront aberration which affects the subjective sharpness; and
a computing device, in communication with or integrated into the wavefront sensor, for:
(i) determining, from the wavefront aberration data, a retinal image quality function which represents an effect of the wavefront aberration on the sharpness;

(ii) providing a neural quality function which represents an effect of neural processing of the subject on the sharpness;

(iii) from the retinal image quality function and the neural quality function, deriving a subjective sharpness metric which represents the subjective sharpness; and (iv) determining a correction for the vision which optimizes the sharpness metric, wherein the computing device performs step (iii) by convolving the retinal image quality function by the neural quality function to form a convolution, wherein the neural quality function represents a response of the subject's retina and brain, and wherein the neural quality function further represents a variation in sensitivity of the eye to edges at horizontal, vertical and oblique orientations.

20. An apparatus for determining an optimal correction for vision of a subject, the apparatus comprising:

a wavefront sensor for taking wavefront aberration data from an eve of the subject, the wavefront aberration data representing a wavefront aberration which affects the subjective sharpness; and a computing device, in communication with or integrated into the wavefront sensor, for:

(i) determining, from the wavefront aberration data, a retinal image quality function which represents an effect of the wavefront aberration on the sharpness;

(ii) providing a neural quality function which represents an effect of neural processing of the subject on the sharpness;

(iii) from the retinal image quality function and the neural quality function, deriving a subjective sharpness metric which represents the subjective sharpness; and (iv) determining a correction for the vision which optimizes the sharpness metric, wherein the computing device performs step (iii) by convolving the retinal image quality function by the neural quality function to form a convolution, wherein the subjective sharpness metric is multivariate.

* * * * *

UNITED STATES PATENT AND TRADEMARK OFFICE
CERTIFICATE OF CORRECTION

PATENT NO. : 7,077,522 B2  Page 1 of 1
APPLICATION NO. : 10/428159
DATED : July 18, 2006
INVENTOR(S) : David R. Williams It is certified that error appears in the above-identified patent and that said Letters Patent is hereby corrected as shown below:

On the Title page, Item (22), "Aug. 29, 2003" should read --May 2, 2003--

Signed and Sealed this

Twenty-fourth Day of March, 2009

JOHN DOLL
*Acting Director of the United States Patent and Trademark Office*